March 29, 1955 J. G. DU PUIS Plant Pat. 1,369
AVOCADO TREE
Filed Jan. 22, 1953
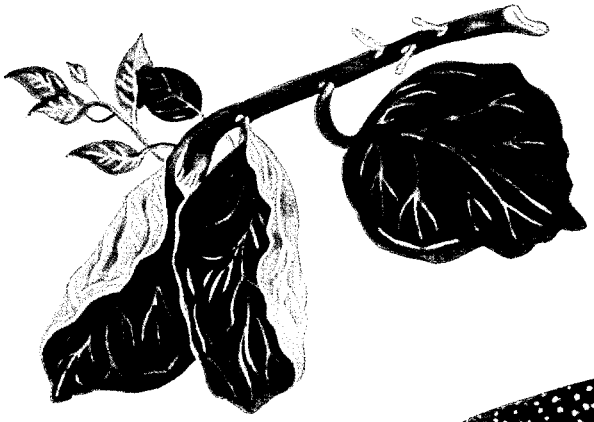
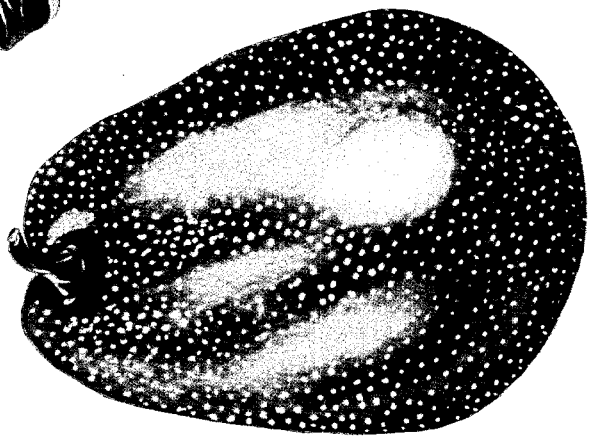
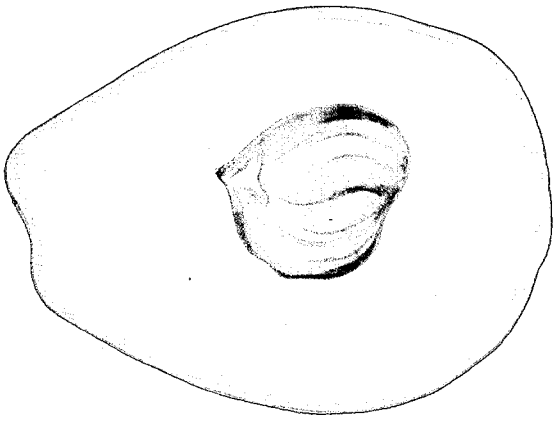
INVENTOR.
BY John G. DuPuis.
Anderson & Ball
ATTORNEYS United States Patent Office Plant Pat. 1,369
Patented Mar. 29, 1955

1,369

AVOCADO TREE

John G. Du Puis, Miami, Fla.

Application January 22, 1953, Serial No. 332,785

1 Claim. (Cl. 47—62)

This invention pertains to a new and distinct variety of avocado tree and fruit, which tree and fruit have certain highly desirable characteristics. During the early part of the avocado season in Florida, namely June and July, the market desires an attractive smooth-skinned large avocado fruit with a relatively small seed, tight in its seed cavity, with a yellow flesh and the quality of shipping some distance to market. The flesh quality must be high to compete with off-shore fruit.

From the viewpoint of the grower, trees should be not too spreading and relatively upright to alleviate crowding in the grove and allow for adequate cultivation. It should be a vigorous growing type relatively resistant to the more common diseases such as scab. Blooming should be early to help insure earlier maturity and the trees should have the inherent ability to set heavy but well-distributed crops of fruit each year.

The tree of my new variety answers all of the general specifications listed above plus others. The tree exhibits acceptable vigor; buds and grafts of this tree on different rootstocks produced young plants of excellent vigor. Several larger trees topworked with graftwood from this tree also exhibit excellent vigor and have produced good crops of uniform fruit each year.

My new variety originated in my grove at Miami, Florida, from a cross made by me between two seedlings developed from seeds of unknown parentage but probably of West Indian origin. I planted the original seed, selecting one of the seedlings which produced unusually fine fruit. I then planted a seed from this seedling, along with others in a new grove. When the quality of the fruit of this selected seedling was evident several years later, I crossed the seedling with another seedling of unknown parentage (probably also of West Indian origin) in my original grove. The new variety resulting from this cross was asexually reproduced by budding and grafting performed by me in my grove in Miami, without apparent variation from the original cross.

Accompanying illustrations show in approximately true colors, a specimen of the fruit, a cross-section of another specimen, and a small twig with both new and mature leaves.

The new variety of avocado tree to which this invention is directed is a tree of moderately upright, compact growth, symmetrical with evenly distributed branches. It does not shoot directly upward as does the Lula nor is it spreading such as the Linda. The foliage of the tree is quite distinctive in that the leaves are almost obovate, opening flat, evenly alternately spaced on the twigs and on all green wood have plump buds at the leaf axils. The leaf tip is obtuse with a small acuminate point. The base of the leaf is wedge-shaped. The margins of the leaf are entire with an occasional slight undulation. On the upper surface of the leaves, the main veins are lighter colored green than the lamina and quite distinct.

Young leaves are reddish exhibiting shades from Old Gold to Maple Sugar (Maerz and Paul, Dictionary of Color, Plate 14, H–I–J–K–L, 5–6–7–8) with distinct veining in the range of Apple Green or Sea Green (Plate 19 J–K–L, 6–7). Under-side of the leaves has a similar color range only in a duller shade.

Mature leaves are glossy on the upper surface and range somewhat lighter than Hunter Green (Plate 24, J–L, 8–9–10). Under sides are dull, a shade lighter than Tarragon (Plate 21, B, 6). The stems are glossy, darker than Pea Green (Plate 20, J, 8) with only an occasional lenticel. Blooming takes place in early spring (February). The flowers appear both as terminal and axillary clusters of indeterminate growth with complete flowers and the characteristic dichogamy of other *Persea americanas*.

One of the outstanding characteristics of this new variety is its ability to set and hold a well-distributed crop of young fruits. The heavy drop during this setting period of many avocado varieties makes them undesirable as commercial crops. Even protracted dry spells or excessive rainfall during a fruit setting period, does not cause an excessive drop in my variety. The fruit matures from the middle of June to the end of July.

The fruit is plumply pyriform with a smooth Peppermint to Harlequin Green skin (Plate 17, J–K, 10–11) with scattered light cream-colored stomata offering an attractive appearance. The heavy, strong stem button is set in a slight depression. The stem is relatively short, 1 to 1½ inches long, firmly attached both to the fruits and branchlet. Fruit vary in size from 24 to 26 ounces, varying in length from 5 to 6 inches and in breadth from 4 to 4½ inches. The seed is small for this size fruit, almost round and coming to a small point at the proximal end, covered with a light brown closely adhering covering, and fits tightly in the seed cavity. The flesh of the fruit is firm, free from fiber and of a delicate nutty flavor. The color is Yellowish (Plate 17, J, 2) shading to a light Green next to the skin.

The distinguishing characteristics of the tree of this invention, are the distinctive appearance of the fruit with its high market quality; the ability to set and hold fruit even during adverse weather condiitons; symmetrical semi-upright growth allowing for easy grove culture; its resistance to avocado scab as brought out by observations and tests in the nursery; its early season maturity; and relatively small seed. It is readily understood that during different seasons or perhaps in different localities the growth habits might vary within the range of common error but the description as given is true. The tree could be recommended for planting in the lower east coast region of Florida as well as the off-shore islands to the east and south.

Having thus disclosed my invention, I claim:

The new and distinct variety of avocado tree, substantially as herein shown and described, characterized particularly by its moderately upright compact growth, symmetrical with evenly distributed branches and leaves almost obovate with small acuminate points; a flowering period occurring early in the spring (February); fruit maturing season each year from the middle of June to the end of July; the ability to set and hold fruit under adverse weather conditions; the fruit being further characterized as plumply pyriform, having smooth green skin with scattered light cream-colored stomata, seed that is relatively small, and flesh which is firm and free from fibre and of a delicate nutty flavor.

No references cited.